United States Patent [19]

Ichikawa et al.

[11] Patent Number: 4,466,954

[45] Date of Patent: Aug. 21, 1984

[54] ORAL COMPOSITION

[75] Inventors: Hiromichi Ichikawa, Matsudo; Kazuo Saso, Hiratsuka; Nobuo Suganuma, Funabashi, all of Japan

[73] Assignee: Lion Corporation, Tokyo, Japan

[21] Appl. No.: 427,542

[22] Filed: Sep. 29, 1982

[30] Foreign Application Priority Data

Dec. 29, 1981 [JP] Japan .................................. 56-213094

[51] Int. Cl.³ .......................... A61K 7/16; A61K 7/28
[52] U.S. Cl. ........................................ 424/50; 424/49; 424/56
[58] Field of Search ..................................... 424/50, 56

[56] References Cited

U.S. PATENT DOCUMENTS

| | | | |
|---|---|---|---|
| 2,812,284 | 11/1957 | Sanders | 424/56 |
| 3,574,824 | 4/1971 | Echeandia et al. | 424/50 |
| 3,622,661 | 11/1971 | King et al. | 424/50 |
| 3,692,894 | 9/1972 | Amo et al. | 424/56 |
| 3,702,805 | 11/1972 | Ishibashi et al. | 424/50 |
| 3,981,989 | 9/1976 | Suganuma et al. | 424/50 |
| 4,082,841 | 4/1978 | Pader | 424/50 |
| 4,150,151 | 4/1979 | Pader et al. | 424/56 |
| 4,264,580 | 4/1981 | Barberio | 424/56 |

*Primary Examiner*—Shep K. Rose
*Attorney, Agent, or Firm*—Birch, Stewart, Kolasch & Birch

[57] ABSTRACT

A stable dextranase-containing oral composition having a good feeling upon use is disclosed which comprises a dextranase enzyme produced by the genus Chaetomium, one of fungi, and a stabilizing amount of an admixture comprising water-soluble salts of alkyl sulfates having 10, 12, 14, and 16 carbon atoms in the alkyl chain in the following proportion:

| | |
|---|---|
| $C_{10}$—alkyl sulfate salt | 0–20%, |
| $C_{12}$—alkyl sulfate salt | 50–80%, |
| $C_{14}$—alkyl sulfate salt | 10–30%, and |
| $C_{16}$—alkyl sulfate salt | 0–15%, | based on the weight of the admixture.

5 Claims, No Drawings

ORAL COMPOSITION

BACKGROUND OF THE INVENTION

This invention relates to dextranase-containing oral compositions such as dentifrices, mouthwashes or the like, and more particularly, to such oral compositions capable of keeping dextranase effective and stable for a long period of time and providing a pleasant sensation during use.

It is well known in the art to incorporate dextranase in oral compositions such as dentifrices as an active ingredient for caries prophylaxis to prevent the formation of dental plaque. For examples, U.S. Pat. Nos. 3,574,824, 3,622,661, 3,686,393, 3,751,561, 3,981,989, 3,991,177, 4,115,546, 4,140,758 and 4,150,113, British Patent Nos. 1,373,003 and 1,427,300, and German Patent No. 1,948,469 disclose dextranase-containing oral compositions.

Inconveniently, dextranase tends to be deactivated by moisture, anionic surfactants and other ingredients in oral compositions. A number of approaches were proposed to keep dextranase stable in oral compositions, but none of them could successfully stabilize dextranase particularly when the oral compositions were stored at elevated temperatures. There is a need for a method capable of keeping dextranase more stable in oral compositions.

Oral compositions such as dentifrices, because of their intended use in the mouth, should preferably taste good and provide high foaming properties to ensure a pleasant mouth feel. Furthermore, for dentifrices, particularly toothpastes, it is desired that a creamy or gel mass be smoothly extrudable from a collapsible tube. Most masses tend to deteriorate in extrudability when aged for a long time at low temperatures. Smooth extrusion from a tube at low temperatures is thus one of the important requirements for dentifrices.

SUMMARY OF THE INVENTION

An object of the present invention is to provide a dextranase-containing oral composition in which dextranase is kept stable for a long period of time.

Another object of the present invention is to provide a dextranase-containing oral composition giving a pleasant sensation during use.

Making extensive investigations to provide an oral composition capable of keeping dextranase stable for a long time and giving a pleasant sensation during use, the inventors have found that this object can be achieved by selecting a dextranase enzyme produced by a fungi of the genus Chaetomium and combining with it a particular admixture of water-soluble salts of alkyl sulfates having restricted numbers of carbon atoms in the alkyl chain.

A number of organisms are known in the art which can produce dextranase enzymes, for example, organisms of Penicillium (Japanese Patent Publication No. 50-20154), Flavobacterium (Japanese Patent Publication No. 50-20155), Helminthosporium (Japanese Patent Publication No. 47-34150), Chaetomium (Japanese Patent Publication No. 46-42955), Gibberella, Gloeosporium, and Glomerella (these three from Japanese Patent Publication No. 47-50391), Fusarium (Japanese Patent Publication No. 47-34149), Brevibacterium (Japanese Patent Publication No. 47-37029), Paecilomyces (Japanese Patent Publication No. 47-34148), Streptomyces (Japanese Patent Publication No. 47-7345), Humichora, Sporotrichum, Anixiella, and Acrosperum (these four from Japanese Patent Publication No. 47-10033). Aspergillus, Verticillium, Spicaria, Carpentelece and Talaromyces are also known. Most of the dextranase enzymes produced by these organisms are generally prone to deactivation in anionic surfactant/water systems. Unexpectedly, the inventors have found that if a dextranase enzyme produced by a fungi of the genus Chaetomium is selected among these dextranase enzymes, a mixture of water-soluble salts of alkyl sulfates is selected as the anionic surfactant, the mixture comprising those water-soluble salts of alkyl sulfates having 10, 12, 14, and 16 carbon atoms in the alkyl group in amounts of 0–20%, 50–80%, 10–30%, and 0–15% (percents being by weight), respectively, and the Chaetomium-produced dextranase together with the mixture of the particular alkyl sulfate salts are blended in an aqueous oral composition such as toothpastes, then the above-mentioned Chaetomium-produced dextranase is not significantly deactivated even at elevated temperatures in the anionic surfactant/water systems, allowing the dextranase to be kept stable and active for a long time. It has also been found that the Chaetomium-produced dextranase has a higher activity than those dextranase enzymes produced by the other organisms. The combination of the present invention allows the dextranase to continuously exert its increased activity for a prolonged period of time. In addition, the thus prepared oral compositions are suitable for application in the mouth as they are excellent in taste, foaming property and mouth feel. Particularly, toothpastes containing the above-mentioned combination are stable at low temperatures and can be smoothly extruded from a tube even after being stored at low temperatures for a long time. These characteristics suggest that the resultant oral compositions such as dentifrices are of high quality. Based on these findings, the inventors have arrived at the present invention.

Therefore the present invention is directed to an oral composition containing dextranase. According to the present invention, a dextranase enzyme produced by a fungi of the genus Chaetomium is used as the dextranase component in combination with a stabilizing amount of an admixture comprising water soluble salts of alkyl sulfates having 10, 12, 14, and 16 carbon atoms in the alkyl group in the following proportion:

| | |
|---|---|
| $C_{10}$—alkyl sulfate salt | 0–20%, |
| $C_{12}$—alkyl sulfate salt | 50–80%, |
| $C_{14}$—alkyl sulfate salt | 10–30%, and |
| $C_{16}$—alkyl sulfate salt | 0–15%, | based on the weight of the admixture. The oral composition containing this combination is improved in stability and activity of dextranase and gives a pleasant sensation during use.

The above and other objects, features and advantages of the present invention will become more apparent and understandable from the following description.

DETAILED DESCRIPTION OF THE INVENTION

The dextranase enzyme used in the dextranase-containing oral compositions of the present invention includes those dextranase enzymes which are produced by the fungi of the genus Chaetomium. This type of dextranase may be prepared by following the procedure described in Japanese Patent Publication No. 46-42192, for example, except that the organism used is replaced by the genus Chaetomium. The dextranase enzyme prepared by this procedure has a titer generally ranging from $10^5$ units to $5 \times 10^7$ units per gram, and thus is effective for the purpose of the present invention. According to the present invention, such as dextranase enzyme produced by the genus Chaetomium is combined with a specific admixture of alkyl sulfate salts, resulting in oral compositions in which the dextranase remains active and stable for a long time. On the other hand, those dextranase enzymes produced by fungi of other genuses, for example, of Penicillium, Aspergillus, Streptomyces, Sporotrichum, Bacillus, etc. are not only lower in activity than the Chaetomium-produced dextranase, but also remain unstable even when combined with the specific admixture of alkyl sulfate salts selected for the present invention, falling to attain the objects of the present invention.

The above-mentioned Chaetomium-produced dextranase may be blended in oral compositions in amounts of 100 to 100,000 units, and more preferably in amounts of 1,000 to 50,000 units per gram of the compositions. It is to be noted that one unit is the amount of enzyme which produces free reducing sugars corresponding to 1 μg of glucose per minute when the reaction is effected in a substrate of dextran.

The admixture of alkyl sulfate salts which can be used in the present invention comprises water-soluble salts of alkyl sulfates having 10, 12, 14, and 16 carbon atoms in the alkyl chain, more specifically, water-soluble salts of decyl sulfate, lauryl sulfate, myristyl sulfate, and palmityl sulfate in amounts of 0–20% ($C_{10}$), 50–80% ($C_{12}$), 10–30% ($C_{14}$), and 0–15% ($C_{16}$), respectively. By blending an admixture of water-soluble salts of alkyl sulfates having the above-specified distribution of carbon atom number in an oral composition containing the Chaetomium-produced dextranase, the stability of dextranase can be increased and the quality of the composition can be improved. On the contrary, the dextranase cannot be stabilized when salts of alkyl sulfates having a carbon atom number distribution outside the above-defined range are used. For example, admixtures of alkyl sulfate salts containing more than 50% of sodium decyl sulfate, more than 90% of sodium lauryl sulfate, or more than 50% of sodium myristyl sulfate cannot fully stabilize the dextranase. Although admixtures of alkyl sulfate salts containing more than 50% of sodium palmityl sulfate or more than 50% of sodium stearyl sulfate can stabilize the dextranase, oral compositions containing them have extremely reduced foaming property, a disagreeable sensation during use, and poor low-temperature stability. It is thus not recommendable in practice to use them as an activating or foaming agent in oral compositions. It should be noted that these percents are based on the weight of the admixtures.

The above-mentioned admixture may preferably comprise water-soluble salts of alkyl sulfates having 10, 12, 14, and 16 carbon atoms in the alkyl chain in the proportion:

| | |
|---|---|
| $C_{10}$—alkyl sulfate salt | 3–18%, |
| $C_{12}$—alkyl sulfate salt | 60–75%, |
| $C_{14}$—alkyl sulfate salt | 12–25%, and |
| $C_{16}$—alkyl sulfate salt | 0–10%, | based on the weight of the admixture. Further, the admixture may preferably comprises at least 98% by weight of the above-specified salts of alkyl sulfates having 10, 12, 14, and 16 carbon atoms in the alkyl chain, and such admixtures are most effective for the purpose of the present invention.

The water-soluble salts of alkyl sulfates used herein may preferably be sodium and potassium salts, but not limited thereto.

The above-mentioned admixture of alkyl sulfate salts may be blended in oral compositions in amounts of 0.1% to 7%, and particularly, in amounts of 0.3% to 3% by weight based on the total weight of the compositions. Amounts of less than 0.1% are too small to provide foaming power, degrading the mouth feel. Another problem arises in the stability of oral compositions, and particularly, liquid separation until occur in toothpaste compositions. If the amount of the admixture of alkyl sulfate salts is above 7%, the stability of dextranase and the low-temperature stability of the oral compositions such as dentifrices are adversely affected.

The dextranase-containing oral composition of the present invention is used in the form of dentifrices such as toothpaste liquid dentifrices and powder dentifrice, liquid oral refreshers, mouthwashes and the like and thus may further contain other commonly used ingredients depending on a particular type of composition.

For dentifrices, an abrasive may be blended generally in an amount of 20 to 90%, and particularly in an amount of 20–60% for toothpastes, examples of the abrasive including dicalcium phosphate dihydrate and anhydride, calcium primary phosphate, calcium tertiary phosphate, calcium carbonate, calcium pyrophosphate, aluminum hydroxide, alumina, silicic acid anhydride, silica gel, aluminum silicate, insoluble sodium metaphosphate, magnesium tertiary phosphate, magnesium carbonate, calcium sulfate, methyl polymethacrylate, bentonite, zirconium silicate, and synthetic resins, and mixtures thereof. Among these, preferred are those aluminum oxide compounds having the general formula:

$$Al_2O_3 \cdot nH_2O \tag{1}$$

wherein $n \geq 0$, preferably $3 \geq n \geq 0$, that is, alumina and hydrated aluminas. The use of these aluminum oxide compounds as a primary abrasive contributes to further stabilization of dextranase. The preferred aluminum oxide compounds are alpha-alumina and hydrated alpha-aluminas. Among the hydrated alpha-aluminas, gibbsite, bayerite, boehmite, diaspore, etc. are preferred, the former two trihydrates being most preferred because of their mild abrasiveness. The best is gibbsite which is commercially available.

In preparing paste-like compositions, typically toothpastes, a binder may be blended generally in an amount of 0.3 to 5% by weight, including carrageenan, cellulose derivatives such as sodium carboxymethyl cellulose, methyl cellulose, hydroxyethyl cellulose, sodium carboxymethyl hydroxyethyl cellulose, etc., alkali metal alginates such as sodium alginate, propylene glycol alginate, gums such as xanthan gum, tragacanth gum, karaya gum and gum arabic, synthetic binding agents such as polyvinyl alcohol, sodium polyacrylate, carboxyvinyl polymer and polyvinyl pyrrolidone, and inorganic binding agents such as silica gel, aluminum silicate gel, veegum and LAPONITE ®, and mixtures thereof. Particularly when an alkali metal monofluorophosphate is used as an additional active ingredient, carrageenan and an alkali metal alginate may preferably be incorporated to improve the stability and mouth feel of dentifrices.

In preparing paste-like or liquid oral compositions, typically toothpastes and mouthwashes, a humectant may be blended generally in an amount of 10 to 70% by weight, including sorbitol, glycerine, ethylene glycol, propylene glycol, 1,3-butylene glycol, polyethylene glycol, polypropylene glycol, xylitol, maltitol, lactitol, etc., and mixtures thereof. Preferably, 1 to 5% by weight of propylene glycol may be used as a binder disperser. Although larger amounts of propylene glycol used tend to reduce the retentivity of dextranase in an aged composition, a sorbitol-based humectant containing 1 part by weight of propylene glycol per 6 to 60 parts by weight of sorbitol is free of such tendency.

In addition to the above-specified admixture of alkyl sulfate salts, another anionic surfactant may be optionally blended in an amount of 0 to 3% by weight, including sodium salts of higher fatty acids, water-soluble salts of sulfonated monoglycerides of higher fatty acids having 10 to 18 carbon atoms in the fatty acid group, such as sodium lauryl monoglyceride sulfonate and sodium coconut monoglyceride sulfonate, sodium monoglyceride monosulfates of higher fatty acids, olefin sulfonates, paraffin sulfonates, sodium N-methyl-N-palmitoyl touride, sodium N-lauroyl sarcosinate, sodium N-lauroyl-$\beta$-alanine, etc., and mixtures thereof. In addition, one or more nonionic and/or amphoteric surfactants may be used in combination with the anionic surfactant in an amount of 0-5% by weight based on the total weight of the composition. Examples of the nonionic surfactants include alkyrol mono- and di-ethanol amides such as lauroyl mono- and di-ethanol amides, stearyl monoglyceride, sucrose fatty acid esters having 12 to 18 carbon atoms in the fatty acid group such as sucrose monolaurate and dilaurate, lactose fatty acid esters, lactitol fatty acid esters, maltitol fatty acid esters, stearic acid monoglyceride, polyoxyethylene sorbitan monolaurate, polyoxyethylene-hardened castor oil, condensates of sorbitan monostearate with approximately 60 moles of ethylene glycol, condensates of ethylene oxide with propylene oxide, and their derivatives such as polyoxyethylene polyoxypropylene monolauryl ester. Examples of the latter include betaine and amino acid type amphoteric surfactants.

Among the above-listed anionic surfactants, water-soluble salts of N-acyl sarcosinates having 10 to 20 carbon atoms in the acyl group such as sodium N-lauroyl sarcosinate are highly effective in stabilizing dextranase. Therefore, the above-specified admixture of alkyl sulfate salts and an N-acyl sarcosinate provide a preferred combination of anionic surfactants for the present composition. The N-acyl sarcosinate may preferably be blended in an amount of 0.5% or less.

Flavors may also be used alone or in admixture in an amount of 0.1 to 10%, preferably 0.5 to 5% by weight of the combined weight of the composition, for example, menthol, carvone, anethole, eugenol, methyl salicylate, limonene, ocimene, n-decylalcohol, citronellol, $\alpha$-terpineol, methyl acetate, citronellyl acetate, methyl eugenol, cineol, linalool, ethyl linalool, thymol, spearmint oil, peppermint oil, lemon oil, orange oil, sage oil, rosemary oil, cinnamon oil, pimento oil, cinnamon leaf oil, wintergreen oil, clove oil and eucalyptus oil. Also included are a sweetener in an amount of 0 to 1%, preferably 0.01 to 0.5% by weight, for example, sodium saccharin, stevioside, neohesperidin dihydrocalcone, glycyrrhizin, perillartine, thaumatin, aspartyl phenylalanine methyl ester, p-methoxy-cinnamic aldehyde, etc.; a preservative, for example, p-hydroxymethylbenzoic acid, p-hydroxyethylbenzoic acid, p-hydroxypropylbenzoic acid, p-hydroxybutylbenzoic acid, sodium benzoate, lower fatty acid monoglycerides, etc.; and other ingredients, for example, gelatin, peptone, arginine hydrochloride, albumin, casein, titanium dioxide, coloring matters and the like. For example, toothpastes may be prepared by kneading any desired ingredients selected from the foregoing ingredients with a proper amount of water.

Other types of oral composition may also be prepared by selecting any desired ingredients as usual and mixing them by a conventional procedure.

Paste-like and liquid oral compositions may generally have a pH ranging from 5 to 10, but not limited thereto.

In addition to the dextranase, the oral compositions of the present invention may further include other additional active ingredients, for example, enzymes such as amylase, protease, mutanase, lysozyme, bacteriolytic enzyme, lytic enzyme, etc.; alkali metal monofluorophosphates such as sodium monofluorophosphate and potassium monofluorophosphate, fluorides such as sodium fluoride and stannous fluoride, tranexamic acid, $\epsilon$-aminocaproic acid, chlorhexidine salts, aluminum chlorohydroxyallantoinate, dihydroxycholesterol, glycyrrhetinates, glycyrrhetinic acid, glycerophosphate, chlorophyll, sodium chloride, caropeptide, water-soluble inorganic phosphoric acid derivatives, and the like, alone or in admixture. Preferably, alkali metal monofluorophosphates such as sodium monofluorophosphate may be combined with dextranase because they not only stabilize dextranase, but also retain sufficient dextranase in aged dentifrice compositions. In this case, the alkali metal monofluorophosphate may preferably be blended in an amount of 0.1 to 1% by weight. Mutanase coacts with dextranase to provide a synergistic effect of dissolving dental plaque and preventing reformation of dental plaque. Dextranase may advantageously be combined with lytic enzyme to increase the efficacy of the latter. Examples of the water-soluble inorganic phosphate are potassium and sodium salts of orthophosphoric acid, pyrophosphoric acid and polyphosphoric acid while the potassium salts are preferred.

Among the foregoing ingredients, omega-amino acids, having the general formula:

$$NH_2-CH_2-R-COOH \qquad (2)$$

wherein R represents a cyclohexane ring or n—$C_4H_8$, that is, tranexamic acid and $\epsilon$-aminocaproic acid or an alkyl ester or aryl ester derivative thereof may preferably be combined with both the dextranase and the admixture of alkyl sulfate salts to further improve the stability of dextranase. One or more omega-amino acids may be blended in the oral composition in an amount of 0.01–3% by weight. Examples of the alkyl ester and aryl ester derivatives of tranexamic acid and $\epsilon$-aminocaproic acid include hexyl tranexamate, phenyl tranexamate, hexyl $\epsilon$-aminocaproate, and heptyl $\epsilon$-aminocaproate.

In summary, the dextranase-containing oral composition of the present invention uses a dextranase enzyme produced by the genus Chaetomium in combination with a specific admixture of water-soluble salts of $C_{10}$, $C_{12}$, $C_{14}$, and $C_{16}$ alkyl sulfates, providing increased stability of dextranase as well as ensuring a pleasant sensation during use.

The following examples are included merely to aid in the understanding of the invention, and variations may be made by one skilled in the art without departing from the spirit and scope of the invention. Unless otherwise stated, all percents are by weight.

EXAMPLES 1 AND 2 AND COMPARATIVE EXAMPLES 1 TO 9

Toothpastes having the following formulation were prepared using dextranase enzymes and admixtures of sodium alkyl sulfates shown in Table 1.

| Formulation | % by weight |
| --- | --- |
| Dicalcium phosphate | 50 |
| Sorbitol | 20 |
| Sodium saccharin | 0.1 |
| Lauroyl diethanol amide | 1.5 |
| Sodium alkyl sulfates | 1.5 |
| Carrageenan | 1.0 |
| Sodium monofluorophosphate | 0.76 |
| Dextranase ($10^6$ units/g) | 0.2 |
| Flavor | 1.0 |
| Water | Balance |
| | 100.0% |

An organoleptic test was carried out by a panel of 15 specialized members to evaluate the taste and foaming of these toothpaste compositions upon use. The quantity of dextranase in the toothpaste compositions was measured both immediately after preparation and after aging for one month at 40° C., determining the retentivity of dextranase after a one-month 40° C. aging relative to the initial. In addition, each of the toothpaste compositions was encased in an aluminum-laminated tube and aged for one month at −5° C. The extrudability of such an aged toothpaste from the tube was evaluated in comparison with that of a fresh toothpaste.

The results are shown in Table 1. The criterions used for evaluation are as follows.

Retentivity of dextranase (aged 40° C., 1 month)

○: more than 70% of dextranase retained
Δ: 30–70% of dextranase retained
x: less than 30% of dextranase retained Taste ○: not bitter
x: bitter Foaming ○: excellent
Δ: fair
x: poor Low-temperature extrusion (aged −5° C., 1 month)

○: optimum to extrude
x: hard to extrude

Overall evaluation

○: no problem in all aspects
Δ: no problem in all aspects except for somewhat low retentivity of dextranase
x: no commercial value.

TABLE 1

| | Source of dextranase | Number of carbon atoms in alkyl group of sodium alkyl sulfate | | Dextranase retentivity | Taste | Foaming | Low-temp. extrusion | Overall evaluation |
| --- | --- | --- | --- | --- | --- | --- | --- | --- |
| C. Ex. 1 | Penicillium | $C_{10}$–$C_{16}$ mixture A* | 99% | x | ○ | ○ | ○ | x |
| C. Ex. 2 | Yeast | $C_{10}$–$C_{16}$ mixture A* | | x | ○ | ○ | ○ | x |
| C. Ex. 3 | Bacterium | $C_{10}$–$C_{16}$ mixture A* | | x | ○ | ○ | ○ | x |
| Ex. 1 | genus Chaetomium | $C_{10}$–$C_{16}$ mixture A* | | ○ | ○ | ○ | ○ | ○ |
| Ex. 2 | " | $C_{10}$–$C_{16}$ mixture B** | 99% | ○ | ○ | ○ | ○ | ○ |
| C. Ex. 4 | " | $C_8$ | 99% | x | x | Δ | ○ | x |
| C. Ex. 5 | " | $C_{10}$ | 99% | x | x | ○ | ○ | x |
| C. Ex. 6 | " | $C_{12}$ | 97% | Δ | ○ | ○ | ○ | Δ |
| C. Ex. 7 | " | $C_{14}$ | 98.5% | Δ | ○ | ○ | ○ | Δ |
| C. Ex. 8 | " | $C_{16}$ | 99.5% | ○ | ○ | x | x | x |
| C. Ex. 9 | " | $C_{18}$ | 99% | ○ | ○ | x | x | x |

Note:
"Ex." shows "Example", and "C. Ex. " shows "Comparative Example"
*$C_{10}$–$C_{16}$ mixture A has the following distribution of carbon atom number
Sodium salt of $C_{10}$ alkyl sulfate 4%
Sodium salt of $C_{12}$ alkyl sulfate 65%
Sodium salt of $C_{14}$ alkyl sulfate 21%
Sodium salt of $C_{16}$ alkyl sulfate 9%
**$C_{10}$–$C_{16}$ mixture B has the following distribution of carbon atom number
Sodium salt of $C_{10}$ alkyl sulfate 16%
Sodium salt of $C_{12}$ alkyl sulfate 69%
Sodium salt of $C_{14}$ alkyl sulfate 13%
Sodium salt of $C_{16}$ alkyl sulfate 1%

As apparent from the results of Table 1, among dextranase enzymes, that produced by the genus Chaetomium remains most stable in toothpastes. By using the dextranase enzyme produced by the genus Chaetomium in combination with a specific admixture of sodium alkyl sulfates having 10, 12, 14, and 16 carbon atoms in the alkyl chain, the dextranase can be kept stable for a long time in toothpastes. In addition, this combination improves the taste and foaming of toothpastes preparations as well as thw low-temperature extrusion from a tube, resulting is a toothpaste which is easy to extrude and favorable to use.

A variety of dextranase enzymes were evaluated for activity by the following procedure.

Dextranase activity evaluation

A 1-g mass was sampled out of each of the toothpastes of Comparative Examples 1 to 3 and Example 1 and diluted with 4 ml of a phosphoric acid buffer at pH 7.0. The resulting supernatant was added to a dextran substrate at pH 7.0, and the system was allowed to react at 40° C. for 10 minutes to produce a free reducing sugar. The ability to produce free reducing sugar is regarded as the titer of a dextranase enzyme. The titer of a dextranase enzyme produced by the genus Chaetomium is assumed to be 100, and the titers of other dextranase enzymes are computed on this basis. The results are shown in Table 2.

TABLE 2

| Source of dextranase | Titer* | Remarks |
|---|---|---|
| Chaetomium | 100 | Example 1 |
| Penicillium | 91 | Comparative Example 1 |
| Yeast | 91 | Comparative Example 2 |
| Bacterium | 68 | Comparative Example 3 |

*ability to produce reducing sugar at 40° C. for 10 min.

As seen from the results of Table 2, the dextranase enzyme produced by the genus Chaetomium has the highest activity. It is concluded that when a dextranase enzyme produced by the genus Chaetomium is combined with a specific admixture of water-soluble salts of alkyl sulfates, there is obtained a dentifrice composition which has the high activity and stability of dextranase, continues to exert the efficacy of dextranase for a long time, and provides improved dentifrice characteristics.

EXAMPLE 3

Toothpaste

A toothpaste having the following formulation was prepared, and evaluated for various factors by the same procedures as in Example 1.

| Ingredient | % by weight |
|---|---|
| Aluminum hydroxide | 50 |
| Silicic acid anhydride | 3 |
| Propylene glycol | 2 |
| Sorbitol | 20 |
| Sodium alkyl sulfates | 1.0 |
| Lauroyl diethanol amide | 1.5 |
| Carrageenan | 1.0 |
| Gelatin | 0.3 |
| Sodium monofluorophosphate | 0.76 |
| Flavor | 1.0 |
| Sodium saccharin | 0.1 |
| Dextranase ($10^6$ units/g) | 0.2 |
| Water | Balance |
| | 100.0% |
| Dextranase retentivity | ○ |
| Taste | ○ |
| Foaming | ○ |
| Low-temperature extrusion | ○ |

The dextranase enzyme used was that produced by the genus Chaetomium. The admixture of sodium alkyl sulfates used had the following distribution of alkyl carbon atom numbers.

| $C_{10}$ alkyl | 5% |
|---|---|
| $C_{12}$ alkyl | 65% |
| $C_{14}$ alkyl | 18% |
| $C_{16}$ alkyl | 11% |

EXAMPLE 4

Toothpaste

| Ingredient | % by weight |
|---|---|
| Dicalcium phosphate | 40 |
| Sorbitol | 15 |
| Glycerine | 5 |
| Sodium alkyl sulfates | 1.5 |
| Myristoyl diethanol amide | 2.0 |
| Sodium alginate | 1.0 |

| Ingredient | % by weight |
|---|---|
| Gelatin | 0.5 |
| Flavor | 1.0 |
| Sodium saccharin | 0.1 |
| Dextranase ($10^6$ units/g) | 0.3 |
| Water | Balance |
| | 100.0% |
| Dextranase retentivity | ○ |
| Taste | ○ |
| Foaming | ○ |
| Low-temperature extrusion | ○ |

The dextranase enzyme used was that produced by the genus Chaetomium. The admixture of sodium alkyl sulfates used had the following distribution of alkyl carbon atom numbers.

| $C_{10}$ alkyl | 17% |
|---|---|
| $C_{12}$ alkyl | 68% |
| $C_{14}$ alkyl | 13% |
| $C_{16}$ alkyl | 1% |

EXAMPLE 5

Toothpaste

| Ingredient | % by weight |
|---|---|
| Calcium carbonate | 50 |
| Propylene glycol | 3 |
| Sorbitol | 30 |
| Lauroyl sarcosinate | 0.3 |
| Sodium alkyl sulfates | 0.8 |
| Palmitoyl diethanol amide | 1.0 |
| Carrageenan | 0.5 |
| Sodium alginate | 0.5 |
| Tranexamic acid | 0.1 |
| Sodium monofluorophosphate | 0.76 |
| Flavor | 1.0 |
| Sodium saccharin | 0.1 |
| Dextranase ($10^6$ units/g) | 0.1 |
| Water | Balance |
| | 100.0% |
| Dextranase retentivity | ○ |
| Taste | ○ |
| Foaming | ○ |
| Low-temperature extrusion | ○ |

The dextranase enzyme used was that produced by the genus Chaetomium. The admixture of sodium alkyl sulfates used has the following distribution of alkyl carbon atom numbers.

| $C_{10}$ alkyl | 2% |
|---|---|
| $C_{12}$ alkyl | 76% |
| $C_{14}$ alkyl | 15% |
| $C_{16}$ alkyl | 5% |

EXAMPLE 6

Toothpowder

| Ingredient | % by weight |
|---|---|
| Calcium carbonate | 80 |
| Sorbitol | 10 |
| Sodium alkyl sulfates | 1.5 |
| Myristoyl diethanol amide | 1.5 |
| Carrageenan | 0.8 |
| Sodium alginate | 0.3 |
| Gelatin | 0.5 |

-continued

| Ingredient | % by weight |
|---|---|
| Sodium monofluorophosphate | 0.76 |
| Flavor | 1.0 |
| Sodium saccharin | 0.1 |
| Dextranase ($10^6$ units/g) | 1.0 |
| Water | Balance |
| | 100.0% |
| Dextranase retentivity | O |
| Taste | O |
| Foaming | O |

The dextranase enzyme used was that produced by the genus Chaetomium. The admixture of sodium alkyl sulfates used had the following distribution of alkyl carbon atom numbers.

| $C_{10}$ alkyl | 12% |
|---|---|
| $C_{12}$ alkyl | 75% |
| $C_{14}$ alkyl | 11% |
| $C_{16}$ alkyl | 0.5% |

EXAMPLE 7

Toothpaste

| Ingredient | % by weight |
|---|---|
| Silicic acid anhydride | 20 |
| Sorbitol | 35 |
| Glycerin | 30 |
| Sodium alkyl sulfates | 1 |
| Lauroyl diethanol amide | 1.2 |
| Carrageenan | 0.3 |
| Sodium alginate | 0.8 |
| Gelatin | 1.0 |
| ε-Aminocaproic acid | 0.1 |
| Flavor | 1.0 |
| Sodium saccharin | 0.1 |
| Dextranase ($10^6$ units/g) | 0.5 |
| Water | Balance |
| | 100.0% |
| Dextranase retentivity | O |
| Taste | O |
| Foaming | O |
| Low-temperature extrusion | O |

The dextranase enzyme used was that produced by the genus Chaetomium. The admixture of sodium alkyl sulfates used had the following distribution of alkyl carbon atom numbers.

| $C_{10}$ alkyl | 14% |
|---|---|
| $C_{12}$ alkyl | 55% |
| $C_{14}$ alkyl | 25% |
| $C_{16}$ alkyl | 6% |

EXAMPLE 8

Mouthwash

| Ingredient | % by weight |
|---|---|
| Ethanol (90%) | 20 |
| Sodium saccharin | 0.3 |
| Sodium alkyl sulfates | 0.5 |
| Flavor | 1.0 |
| Dextranase (5 × $10^6$ units/g) | 1.0 |
| Water | Balance |
| | 100.0% |
| Dextranase retentivity | O |

-continued

| Ingredient | % by weight |
|---|---|
| Taste | O |

The dextranase enzyme used was that produced by the genus Chaetomium. The admixture of sodium alkyl sulfates used had the following distribution of alkyl carbon atom numbers.

| $C_{10}$ alkyl | 10% |
|---|---|
| $C_{12}$ alkyl | 58% |
| $C_{14}$ alkyl | 28% |
| $C_{16}$ alkyl | 2% |

EXAMPLE 9

Oral refresher

| Ingredient | % by weight |
|---|---|
| Ethanol | 30 |
| Glycerin | 15 |
| Sodium saccharin | 0.3 |
| Sodium alkyl sulfates | 0.1 |
| Flavor | 3.0 |
| Dextranase (2 × $10^6$ units/g) | 0.5 |
| Water | Balance |
| | 100.0% |
| Dextranase retentivity | O |
| Taste | O |

The dextranase enzyme used was that produced by the genus Chaetomium. The admixture of sodium alkyl sulfates used had the following distribution of alkyl carbon atom numbers.

| $C_{10}$ alkyl | 8% |
|---|---|
| $C_{12}$ alkyl | 68% |
| $C_{14}$ alkyl | 16% |
| $C_{16}$ alkyl | 7% |

What is claimed is:

1. An oral composition, comprising:
   100 to 100,000 units per gram of the composition of a dextranase enzyme produced by a fungi of the genus Chaetomium; and
   0.1% to 7% by weight based on the total weight of the composition of an admixture comprising water-soluble salts of alkyl sulfates having 10, 12, 14, and 16 carbon atoms in the alkyl chain in the following proportion:

| $C_{10}$—alkyl sulfate salt | 0–20%, |
|---|---|
| $C_{12}$—alkyl sulfate salt | 50–80%, |
| $C_{14}$—alkyl sulfate salt | 10–30%, and |
| $C_{16}$—alkyl sulfate salt | 0–15%, | based on the weight of the admixture.

2. The oral composition according to claim 1 wherein the admixture comprises water-soluble salts of alkyl sulfates having 10, 12, 14 and 16 carbon atoms in the alkyl chain in the following proportions:

| $C_{10}$—alkyl sulfate salt | 3–18%, |
|---|---|
| $C_{12}$—alkyl sulfate salt | 60–75%, |
| $C_{14}$—alkyl sulfate salt | 12–25%, and |

| | |
|---|---|
| -continued | |
| $C_{16}$—alkyl sulfate salt | 0–10%, | based on the weight of the admixture.

3. The oral composition according to claim 1 or 2 wherein the admixture comprises at least 98% by weight of the water-soluble salts of alkyl sulfates having 10, 12, 14, and 16 carbon atoms in the alkyl chain.

4. The oral composition according to claim 1, wherein dextranase is present in the composition in an amount of 1,000 to 50,000 units per gram of the composition.

5. The oral composition according to claim 1, wherein said admixture of alkyl sulfates is present in an amount of 0.3% to 3% by weight based on the total weight of the composition.

* * * * *